(12) United States Patent
Suzuki et al.

(10) Patent No.: US 9,051,306 B2
(45) Date of Patent: Jun. 9, 2015

(54) INDIRUBIN DERIVATIVE HAVING HIGHLY SELECTIVE CYTOTOXICITY FOR MALIGNANT TUMORS

(75) Inventors: Takashi Suzuki, Ichikawa (JP); Shinichi Miyairi, Koto-ku (JP); Hiroaki Saito, Yachiyo (JP); Keiichi Tabata, Narashino (JP)

(73) Assignee: NIHON UNIVERSITY, Tokyo (JP)

( * ) Notice: Subject to any disclaimer, the term of this patent is extended or adjusted under 35 U.S.C. 154(b) by 0 days.

(21) Appl. No.: 14/232,836

(22) PCT Filed: Jul. 5, 2012

(86) PCT No.: PCT/JP2012/067153
§ 371 (c)(1),
(2), (4) Date: Jan. 14, 2014

(87) PCT Pub. No.: WO2013/011841
PCT Pub. Date: Jan. 24, 2013

(65) Prior Publication Data
US 2014/0200253 A1    Jul. 17, 2014

(30) Foreign Application Priority Data
Jul. 15, 2011   (JP) .................................. 2011-156299

(51) Int. Cl.
C07D 405/14    (2006.01)
A61K 31/336    (2006.01)

(52) U.S. Cl.
CPC ..................................... *C07D 405/14* (2013.01)

(58) Field of Classification Search
CPC ...................................................... C07D 405/14
USPC ........................................................ 548/459
See application file for complete search history.

(56) References Cited

U.S. PATENT DOCUMENTS

| | | |
|---|---|---|
| 2007/0276025 A1 | 11/2007 | Meijer et al. |
| 2008/0194024 A1 | 8/2008 | Mays |
| 2009/0111987 A1 | 4/2009 | Tzeng et al. |

FOREIGN PATENT DOCUMENTS

| | | |
|---|---|---|
| WO | 2002/100401 | 12/2002 |
| WO | 2005/041954 | 5/2005 |
| WO | 2007/117262 | 10/2007 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Adachi, Jun et al., "Indirubin and Indigo Are Potent Aryl Hydrocarbon Receptor Ligands Present in Human Urine", The Journal of Biological Chemistry , vol. 276, No. 34, pp. 31475-31478, 2001.
Damiens, Eve et al., "Anti-mitotic properties of indirubin -3'-monoxime, a CDK/GSK-3 inhibitor: induction of endoreplication following prophase arrest", Oncogene, vol. 20, pp. 3786-3797, 2001.
Dallavalle, Sabrina et al., "Novel 7-Oxyiminomethyl Derivatives of Camptothecin with Potent in Vitro and in Vivo Antitumor Activity", Journal of Medicinal Chemistry, vol. 44, No. 20, pp. 3264-3274, 2001.
Mlochowski, Jacek et al., "Derivatives of 1,10-and 4,7-Phenathrolinaldehydes and Di(N,N-diethylamino)ethoxyphenanthrolines as Potential Antitumor Agents", Journal fuer Praktische Chemie/chemiker-Zeitung, vol. 335, No. 7, pp. 623-627, 1993.
Mlochowski, Jacek et al., "Synthesis of 2,7-Fluorenone Bisglycidyl Ether and Related Compounds as Potential Cytostatics", Journal fuer Praktische Chemie, vol. 332, No. 1, pp. 5-14, 1990.
International Search Report Issued Jul. 31, 2012 in PCT/JP12/067153 Jul. 5, 2012.

* cited by examiner

*Primary Examiner* — Shawquia Jackson
(74) *Attorney, Agent, or Firm* — Oblon, McClelland, Maier & Neustadt, L.L.P.

(57) ABSTRACT

An agent for treating malignant tumors based on a new mechanism is provided, which comprises an indirubin derivative represented by formula (1) or a salt thereof:

(1)

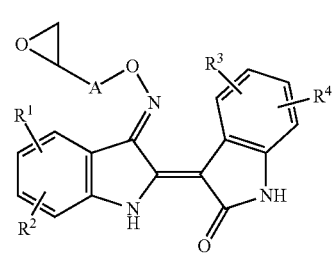

wherein A represents an alkylene group having 1 to 4 carbon atoms, and $R^1$ to $R^4$ each independently represent a hydrogen atom, a halogen atom, a hydroxy group, or an alkoxy group.

10 Claims, 2 Drawing Sheets

INDIRUBIN DERIVATIVE HAVING HIGHLY SELECTIVE CYTOTOXICITY FOR MALIGNANT TUMORS

TECHNICAL FIELD

The present invention relates to a new indirubin derivative or a salt thereof and to a pharmaceutical comprising the derivative or a salt thereof.

BACKGROUND ART

Cancer (malignant tumor) is a disease ranked as the first leading cause of death, for which new therapies are needed. At present, therapies for malignant tumors include surgical therapies, radiotherapies, and chemotherapies (anti-malignant tumor agents), and these therapies are usually combined for treatment. Anticancer agents used include alkylating agents, antimetabolites, alkaloid anticancer agents, anticancer antibiotics, platinum-based drugs, molecular targeted drugs, etc. These anticancer agents still cannot be considered to have a sufficient therapeutic effect and also have the problem of high frequency of side effects.

On the other hand, indirubins, which are indole compounds isolated from human urine, are known to have higher affinity for the aryl hydrocarbon receptor (AhR) than 2,3,7,8-tetrachlorodibenzo-p-dioxin (TCDD), an environmental hormone. Thus, it is suggested that indirubins may be an endogenous ligand for the AhR (Non-Patent Literature 1). It is also reported that indirubins act on cyclin-dependent kinases (CDKs) and glycogen synthase kinase-3β (GSK-3β) to influence cell cycle, cell differentiation, nerve cell polarization, and so on (Non-Patent Literature 2). These target proteins for indirubins are highly involved in cell proliferation, and GSK-3β is a tyrosine kinase which is a target of recent molecular targeted drugs for cancer therapy.

CITATION LIST

Non-Patent Literatures

Non-Patent Literature 1: Adachi, J., Mori, Y., Matsui, S., Takigami, H., Fujino, J., Kitagawa, H., Miller III, C. A., Kato, T., Saeki, K., Matsuda, T., J. Biol. Chem. 2001, 276, 31475.

Non-Patent Literature 2: Damiens, E., Baratte, B., Marie, D., Eisenbrand, G., Meijer, L., Oncogene, 2001, 20, 3786.

SUMMARY OF INVENTION

Technical Problem

It is an object of the present invention to provide an agent for treating malignant tumors based on a new mechanism.

Solution to Problem

Thus, the inventors focused attention on indirubins, which are known to act on CDKs and GSK-3β, a tyrosine kinase which is a target of molecular targeted drugs for cancer therapy, and synthesized various derivatives thereof to examine their cancer cell growth-inhibiting effects. As a result, the inventors accomplished the present invention based on findings that a compound obtained by oximating indirubin at position 3 and further introducing thereto an epoxy group has a stronger cancer cell growth-inhibiting effect than cisplatin conventionally known as a potent agent for treating malignant tumor.

Specifically, the present invention provides an indirubin derivative represented by formula (1), or a salt thereof:

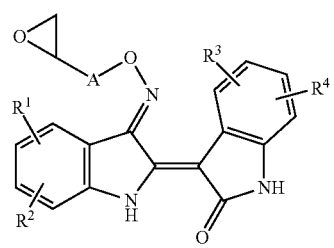

(1)

in the formula, A represents an alkylene group having 1 to 4 carbon atoms, and $R^1$ to $R^4$ each independently represent a hydrogen atom, a halogen atom, a hydroxy group, or an alkoxy group.

The present invention also provides a pharmaceutical, specifically, an agent for treating a malignant tumor or for inducing apoptosis, which comprises the indirubin derivative or a salt thereof as an active ingredient.

The present invention also provides a pharmaceutical composition comprising the indirubin derivative or a salt thereof and a pharmaceutically acceptable carrier.

The present invention also provides use of the indirubin derivative or a salt thereof for the manufacture of a pharmaceutical, specifically, an agent for treating a malignant tumor or for inducing apoptosis.

The present invention also provides the indirubin derivative or a salt thereof for treating a malignant tumor or inducing apoptosis.

The present invention also provides a method of treating a malignant tumor or inducing apoptosis, which comprises administering an effective amount of the indirubin derivative or a salt thereof.

Advantageous Effect of Invention

The indirubin derivative (1) of the present invention can strongly inhibit the growth of malignant tumor cells and is useful as an agent for treating malignant tumors.

DESCRIPTION OF EMBODIMENTS

Figure 1:
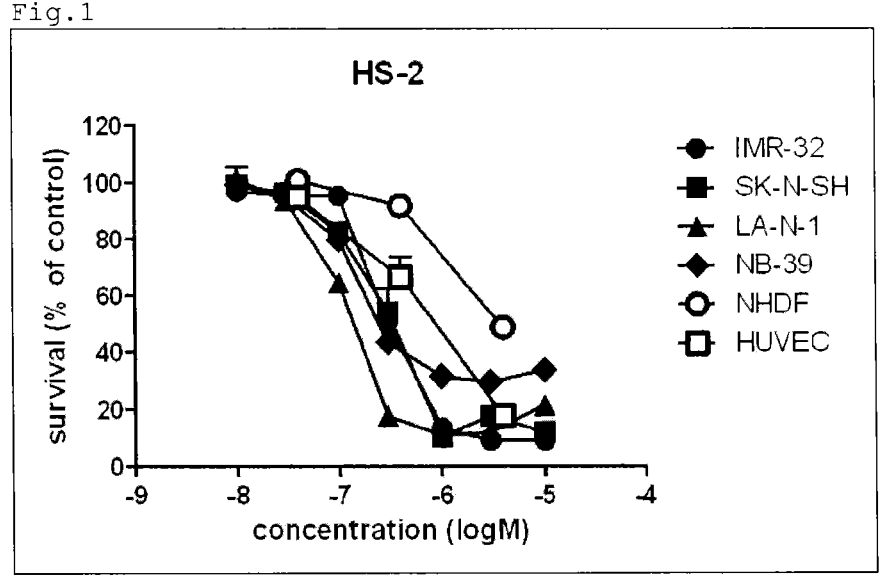
FIG. 1 is a graph showing the cytotoxic activity of a compound of the present invention (HS-2) on neuroblastoma cells IMR-32, SK-N-SH, LA-N-1, and NB-39, in which the horizontal axis represents compound concentration, and the vertical axis represents cell survival rate.

The indirubin derivative of the present invention is represented by formula (1). In formula (1), A represents an alkylene group having 1 to 4 carbon atoms. The alkylene group may be a linear or branched alkylene group such as a methylene group, an ethylene group, a propylene group, a trimethylene group, a tetramethylene group, or a butylene group. Among them, a methylene group or an ethylene group is more preferred, and a methylene group is particularly preferred.

$R^1$ to $R^4$ each independently represent a hydrogen atom, a halogen atom, a hydroxy group, or an alkoxy group. The halogen atom may be a chlorine atom, a fluorine atom, a bromine atom, or an iodine atom. The alkoxy group may be an alkoxy group having 1 to 6 carbon atoms. The alkoxy group is more preferably an alkoxy group having 1 to 4 carbon atoms, such as a methoxy group, an ethoxy group, an isopropyloxy group, an n-propyloxy group, or an n-butyloxy group, particularly preferably a methoxy group or an ethoxy group.

$R^1$ to $R^4$ are preferably a hydrogen atom or an alkoxy group, and particularly preferably a hydrogen atom.

A salt of the indirubin derivative (1) may be an inorganic acid salt such as a hydrochloride, a nitrate, or a sulfate, or an organic acid salt such as an acetate or a fumarate. When having an asymmetric carbon atom or atoms, the indirubin derivative (1) of the present invention may also include an optically active compound and a racemate. The compound of the present invention may also be present in the form of a solvate such as a hydrate.

For example, the indirubin derivative (1) may be produced according to the following reaction formula.

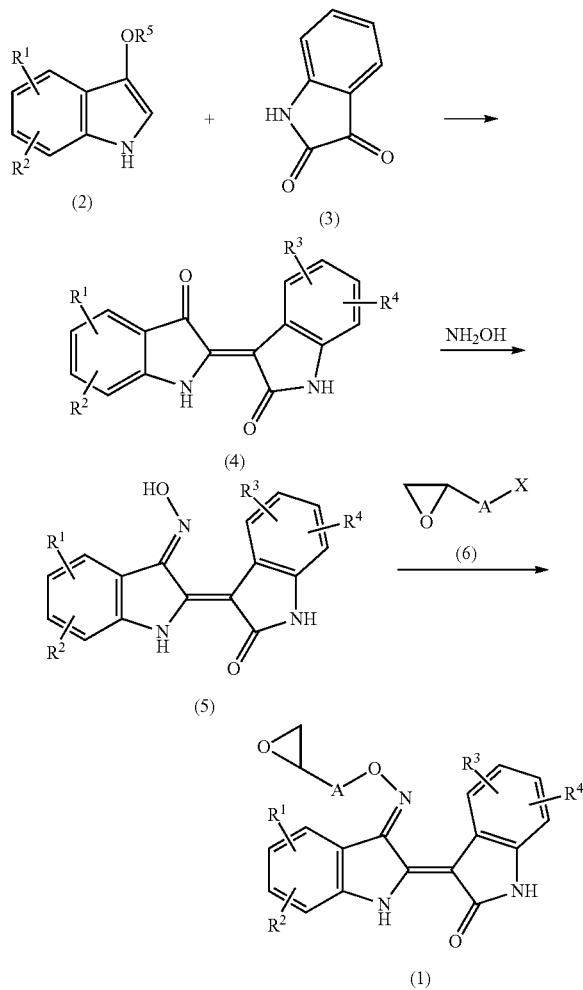

In the formula, $R^5$ represents an alkanoyl group, X represents a halogen atom, and A and $R^1$ to $R^4$ have the same meanings as defined above.

Specifically, an indoxyl carboxylate (2) and an isatin (3) are condensed in the presence of a base to form an indirubin (4). Hydroxylamine or a salt thereof is allowed to react with the indirubin (4) to form indirubin-3'-oxime (5). Subsequently, a haloalkyloxirane (6) is allowed to react with indirubin-3'-oxime (5) to form the indirubin derivative (1).

In the reaction formula, the alkanoyl group represented by $R^5$ may be an acetyl group, a propionyl group, or the like. The halogen atom represented by X may be a chlorine atom, a bromine atom, or the like.

The base used for the reaction between the compounds (2) and (3) may be sodium carbonate, potassium carbonate, sodium hydroxide, or the like. The solvent used for this reaction may be an alcohol solvent such as methanol or ethanol. The reaction may be carried out at room temperature, and the reaction time may be from 10 to 24 hours.

The compound (4) is allowed to react with hydroxylamine or a salt thereof to form the oxime compound (5). This reaction is preferably carried out in a solvent such as pyridine or toluene with heating under reflux.

The halohydrin (6) which the oxime is allowed to react with, may be epibromohydrin, epichlorohydrin, or the like. This reaction may be carried out in the presence of a tertiary amine such as triethylamine, DBU, or DABCO in an aprotic polar solvent such as dimethylformamide at room temperature.

As shown in the examples described below, the indirubin derivative (1) obtained in this way has a strong malignant tumor cell growth-inhibiting effect and also has the ability to induce apoptosis of malignant tumor cells. Therefore, it is useful as an agent for treating malignant tumors.

The agent for treating a malignant tumor of the present invention can be effective against a wide range of malignant tumors, examples of which include epithelial cancers such as pharyngeal cancer, laryngeal cancer, lingual cancer, lung cancer, breast cancer, esophageal cancer, stomach cancer, colon cancer, uterine cancer, ovarian cancer, liver cancer, pancreatic cancer, gallbladder cancer, kidney cancer, prostatic cancer, malignant melanoma, and thyroid cancer; and non-epithelial cancers such as osteosarcoma, chondrosarcoma, rhabdomyosarcoma, leiomyosarcoma, liposarcoma, angiosarcoma, fibrosarcoma, leukemia, malignant lymphoma, and myeloma.

The agent for treating a malignant tumor of the present invention may be, along with a pharmaceutically-acceptable carrier well-known in the art, may be formulated by mixing, dissolving, granulating, tableting, emulsifying, encapsulating, a freeze-drying, or the like.

For oral administration, the indirubin derivative (1) may be, along with a pharmaceutically-acceptable solvent, excipient, binder, stabilizer, dispersant, or other additives, formulated into a dosage form such as a tablet, a pill, a sugar-coated drug, a soft capsule, a hard capsule, a solution, a suspension, an emulsion, a gel, a syrup, or a slurry.

For parenteral administration, the indirubin derivative (1) may be, along with a pharmaceutically-acceptable solvent, excipient, binder, stabilizer, dispersant, or other additives, formulated into a dosage form such as a solution for injection, a suspension, an emulsion, a cream, an ointment, an inhalant, or a suppository. A formulation for injection may be prepared by dissolving the therapeutic agent of the present invention in an aqueous solution, preferably, a physiologically compatible buffer such as a Hanks' solution, a Ringer's solution, or a physiological saline buffer. The composition may also be prepared in a form such as a suspension, a solution, or an emulsion in an oily or aqueous vehicle. Alternatively, the indirubin derivative (1) may be produced in the form of a powder, and an aqueous solution or a suspension may be prepared using the powder and sterilized water or the like before use. For inhalation, the indirubin derivative (1) may be powdered and mixed with an appropriate base such as lactose or starch to form a powder mixture. A suppository formulation may be produced by mixing the indirubin derivative (1) with a common suppository base such as cacao butter. The therapeutic agent of the present invention may also be embedded in a polymer matrix or other materials to form a sustained release preparation.

For example, the dosage of the indirubin derivative (1) is preferably from 1 mg to 500 mg per day for an adult, depending on administration route, the condition, weight, and age of the patient, and other factors.

The agent for treating a malignant tumor of the present invention is generally administered by a parenteral route, such as injection (such as subcutaneous injection, intravenous injection, intramuscular injection, or intraperitoneal injection), transdermal route, transmucosal route, transnasal route, or transpulmonary route. However, there is no particular limitation, and the agent may also be orally administered.

EXAMPLES

Next, the present invention will be more specifically described with reference to examples, which, however, are not intended to limit the present invention.

Example 1

(1) Production of Indirubin

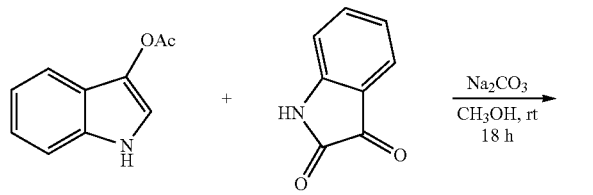

Argon gas was blown into a suspension of indoxyl acetate (1.75 g, 10 mmol) and isatin (1.47 g, 10 mmol) in anhydrous methanol (20 mL) for 5 minutes. Sodium carbonate (2.12 g, 20 mmol) was added to the reaction liquid and stirred at room temperature for 18 hours. The reaction liquid was then poured into water (1 L). The precipitated crude crystals were collected by suction filtration. The resulting crude crystals were recrystallized from 1,4-dioxane/hexane to give purple needle-shaped crystals of indirubin (1.81 g, 69%).

$^1$H NMR (DMSO-$d_6$): δ 6.91 (1H, d, J=7.3 Hz, 7-H), 7.02 (2H, m, 5-H, and 5'-H), 7.26 (1H, dt, J=7.3, 1.2 Hz, 6-H), 7.42 (1H, d, J=8.1 Hz, 7'-H), 7.58 (1H, dt, J=8.1, 1.2 Hz, 6'-H), 7.66 (1H, dd, J=7.1, 1.2 Hz, 4'-H), 8.77 (1H, dd, J=7.8, 1.2 Hz, 4-H), 10.90 (1H, s, 1-H), 11.02 (1H, s, 1'-H). LRMS (EI): 262 ([M]$^+$). HRMS calcd for $C_{16}H_{10}N_2O_2$: 262.0742, found: 262.0740.

(2) Production of indirubin-3'-oxime

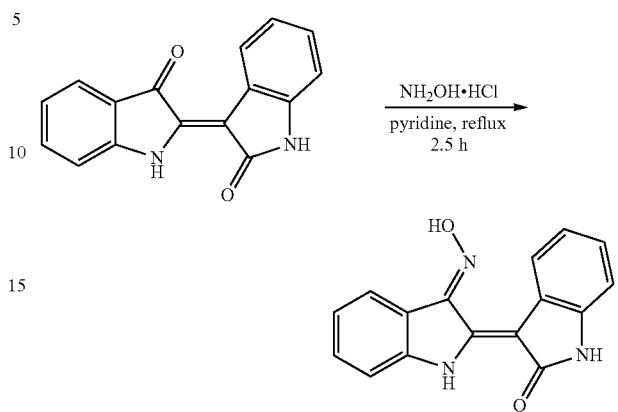

Indirubin (0.64 g, 2.4 mmol) was dissolved in anhydrous pyridine (25 mL), and hydroxylammonium chloride (1.67 g, 24 mmol) was added to the solution. The reaction liquid was heated and refluxed for 2.5 hours and then cooled to room temperature. The reaction liquid was poured into water (100 mL), and the precipitated crude crystals were collected by suction filtration. The resulting crude crystals were recrystallized from methanol/water to give red needle-shaped crystals of indirubin-3'-oxime (0.60 g, 89%).

$^1$H NMR (DMSO-$d_6$): δ 6.89 (1H, d, J=7.8 Hz, 7-H), 6.95 (1H, dt, J=7.8, 0.9 Hz, 5-H), 7.03 (1H, m, 5'-H), 7.13 (1H, dt, J=7.8, 0.9 Hz, 6-H), 7.40 (2H, m, 6'- and 7'-H), 8.24 (1H, d, J=6.9 Hz, 4'-H), 8.65 (1H, d, J=7.8 Hz, 4-H), 10.71 (1H, s, 1-H), 11.75 (1H, s, 1'-H), 13.48 (1H, s, NOH). LRMS (EI): 277 ([M]$^+$). HRMS calcd for $C_{16}H_{11}N_3O_2$: 277.0851, found: 277.0848.

(3) Production of indirubin-3'-(O-oxiran-2-ylmethyl)oxime (HS-2)

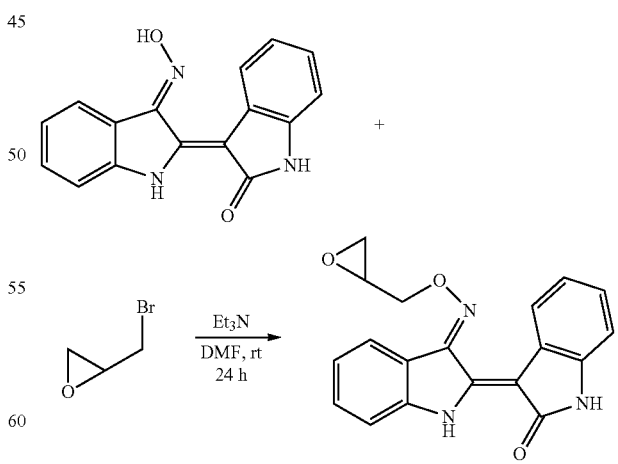

Indirubin-3'-oxime (100 mg, 0.36 mmol) was dissolved in anhydrous DMF (5 mL), and triethylamine (0.1 mL) and epibromohydrin (0.5 g, 3.6 mmol) were sequentially added to the solution. The mixture was stirred at room temperature for 24 hours. The reaction mixture was poured into water (50 mL), and the product was collected by suction filtration to give the title compound (HS-2) (95 mg, 79%). The product was determined to be pure by TLC and NMR.

$^1$H NMR (DMSO-$d_6$): δ 2.84 (1H, dd, J=4.9, 2.6 Hz, one of CH(O)CH$_2$), 2.98 (1H, t, J=4.9 Hz, one of CH(O)CH$_2$), 3.52 (1H, m, CH(O)CH$_2$), 4.55 (1H, dd, J=12.4, 6.1 Hz, one of NOCH$_2$CH), 4.82 (1H, dd, J=12.4, 3.5 Hz, one of NOCH$_2$CH), 6.97 (1H, d, J=7.2 Hz, 7-H), 7.01 (1H, d, J=7.8 Hz, 7'-H), 7.03 (1H, t, J=7.8 Hz, 5-H), 7.09 (1H, dt, J=7.8, 1.2 Hz, 5'-H), 7.20 (1H, dt, J=7.8, 1.2 Hz, 6-H), 7.39 (1H, dt, J=7.8, 1.2 Hz, 6'-H), 7.70 (1H, s, 1-H), 8.23 (1H, d, J=7.7 Hz, 4'-H), 8.69 (1H, d, J=7.8 Hz, 4-H), 11.56 (1H, s, 1'-H). LRMS (EI): 333 ([M]$^+$). HRMS calcd for $C_{19}H_{15}N_3O_3$: 333.1113, found: 333.1113.

Example 2

Antitumor Activity (1)

Antitumor activity was determined by the MTT (3-(4,5-dimethylthiazol-2-yl)-2,5-diphenyltetrazolium bromide) method.

One hundred μL of a suspension of tumor cells in an RPMI 1640 medium was seeded into a 96-well plate (1×10$^4$ cells/well) and cultured for 24 hours (5% $CO_2$, 37° C., saturated humidity conditions). Subsequently, the test compound (final concentration of from 1×10$^{-5}$ to 1×10$^{-8}$ M) and DMSO as a control were each added in an amount of 0.2 μL and allowed to act on the tumor cells for 48 hours. Subsequently, 10 μL of a 0.5% MTT solution was added. After 3 hours, 100 μL of a reaction terminating solution (0.04 N HCl/isopropanol) was added to terminate the reaction. After thorough pipetting, the absorbance was measured at 570 nm (top) and 655 nm (bottom) using a microplate reader. The cell survival rate for each sample at each concentration was calculated as a percentage to the control group, and IC$_{50}$ values were determined from the data. The tumor cells used were human neuroblastoma cells IMR-32, SK-N-SH, LA-N-1, and NB-39 and human liver cancer cells HepG-2. Non-tumor cells: normal human dermal fibroblasts (NHDF) and human umbilical vein endothelial cells (HUVEC) were also used.

FIG. 1 and Table 1 show the antitumor activity of the compound (HS-2) of the present invention. It has been found from FIG. 1 and Table 1 that the compound of the present invention has strong antitumor activity and that its antitumor activity is 50 to 100 times stronger than that of cisplatin (CDDP).

TABLE 1

|  | IC$_{50}$ (μM) | |
| --- | --- | --- |
|  | HS-2 | CDDP |
| IMR-32 | 0.329 | 28.2 |
| SK-N-SH | 0.325 | 12.1 |
| NB-39 | 0.550 | 2.04 |
| LA-N-1 | 0.139 | 1.63 |
| HepG-2 | 1.00 | 10.0 |
| NHDF | 61.4 | >100 |
| HUVEC | 1.75 | 69.8 |

Example 3

Antitumor Activity (2)

(1) Culture Medium
Fetal bovine serum (FBS) was added at a final concentration of 10% to dulbecco's modified eagle's medium (DMEM, Sigma-Aldrich), and a penicillin-streptomycin solution (GIBCO) was further added at a concentration of 0.1 mg/mL.

(2) Reagent
An Alamar Blue solution manufactured by Wako Pure Chemical Industries, Ltd. was used.

(3) Procedure
One hundred μL aliquot of a suspension of human liver cancer cell line HepG2 cells in DMEM medium (1.0×10$^5$ cells/mL) was dispensed into a 96-well culture plate. The cells were allowed to adhere to the plate by being cultured at 37° C. in 5% $CO_2$ under saturated humidity conditions. After culture for 24 hours, the medium was removed by suction, and 100 μL of a test compound-containing medium (containing 1% DMSO) was added. The cells were cultured at 37° C. in 5% $CO_2$ under saturated humidity conditions. After culture for 24 hours, the medium was removed by suction, and the cells were washed with phosphate buffered saline (PBS). The Alamar Blue reagent solution (100 μL) diluted 10 times with the medium was added to each well, and the cells were cultured under the same conditions. After 1 hour, the fluorescence intensity was measured at an excitation wavelength of 577 nm and a detection wavelength of 612 nm. When the cell survival rate was calculated, the value for the well added with the vehicle (containing 1% DMSO) was normalized as 100%.

(4) Results
Against human liver cancer cell line HepG2, HS-2 showed cytotoxic activity (IC$_{50}$: 50% inhibitory concentration) at 1.0 μM, while cisplatin (CDDP) showed cytotoxic activity at 10 μM.

Example 4

Ability to Induce Apoptosis (Hoechst 33342 Staining Method)

The ability to induce apoptosis was examined using nuclear staining by the Hoechst 33342 staining method.

Figure 2:
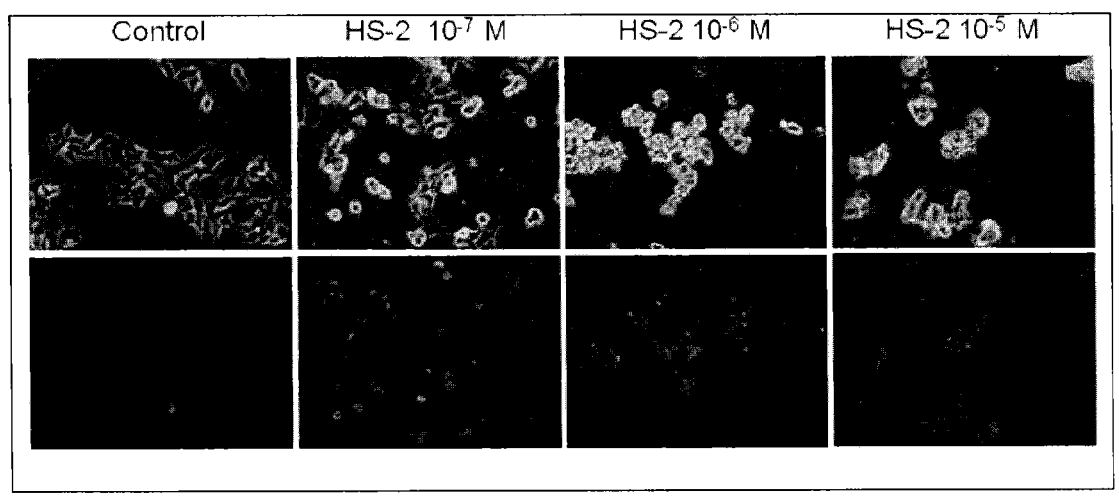
FIG. 2 shows that a compound of the present invention (HS-2) induced apoptosis of IMR-32 neuroblastoma cells.

Two mL of a suspension of cells (IMR-32) in an RPMI 1640 medium was seeded into a 6-well plate (1×10$^5$ cells/well) and cultured for 24 hours (under 5% $CO_2$, 37° C., and saturated humidity conditions). Subsequently, the test compound (final concentration of from 1×10$^{-5}$ M to 1×10$^{-7}$ M) and DMSO as a control were each added in an amount of 4 μL and allowed to act on the cells for 24 hours. Subsequently, 100 μL of a 0.02% Hoechst 33342 solution was added. After 15 minutes, phase-contrast images and fluorescence images of the cells were taken with a fluorescence microscope to observe changes in cell morphology. As a result, it was found that the cytotoxic activity on the IMR-32 cells was caused by induction of apoptosis because, as shown in FIG. 2, the compound (HS-2) of the present invention induced nuclear aggregation and fragmentation at 0.1 μM.

Example 5

Ability to Induce Apoptosis (Flow Cytometry Technique)

Flow cytometry was used to detect whether the compound (HS-2) of the present invention had the ability to induce apoptosis of human neuroblastoma IMR-32 cells. Specifically, 2 mL of a suspension of cells (IMR-32) in an RPMI 1640 medium was seeded into a 6-well plate (1×10$^6$ cells/well) and cultured for 24 hours (under 5% $CO_2$, 37° C., and saturated humidity conditions). Subsequently, the compound (HS-2) was added at a final concentration of from 1×10$^{-5}$ M to 1×10$^{-7}$ M and incubated under 37° C. and 5% $CO_2$ conditions for 24 hours. The cells were detached with trypsin and washed with PBS. Annexin V-FITC and propidium iodide (PI) were then added to the cells to carry out flow cytometry. In this technique, only Annexin V-FITC fluorescence is observed from cells in the early apoptosis phase, and both Annexin V fluorescence and PI fluorescence are observed from cells in the late apoptosis phase.

Figure 3:
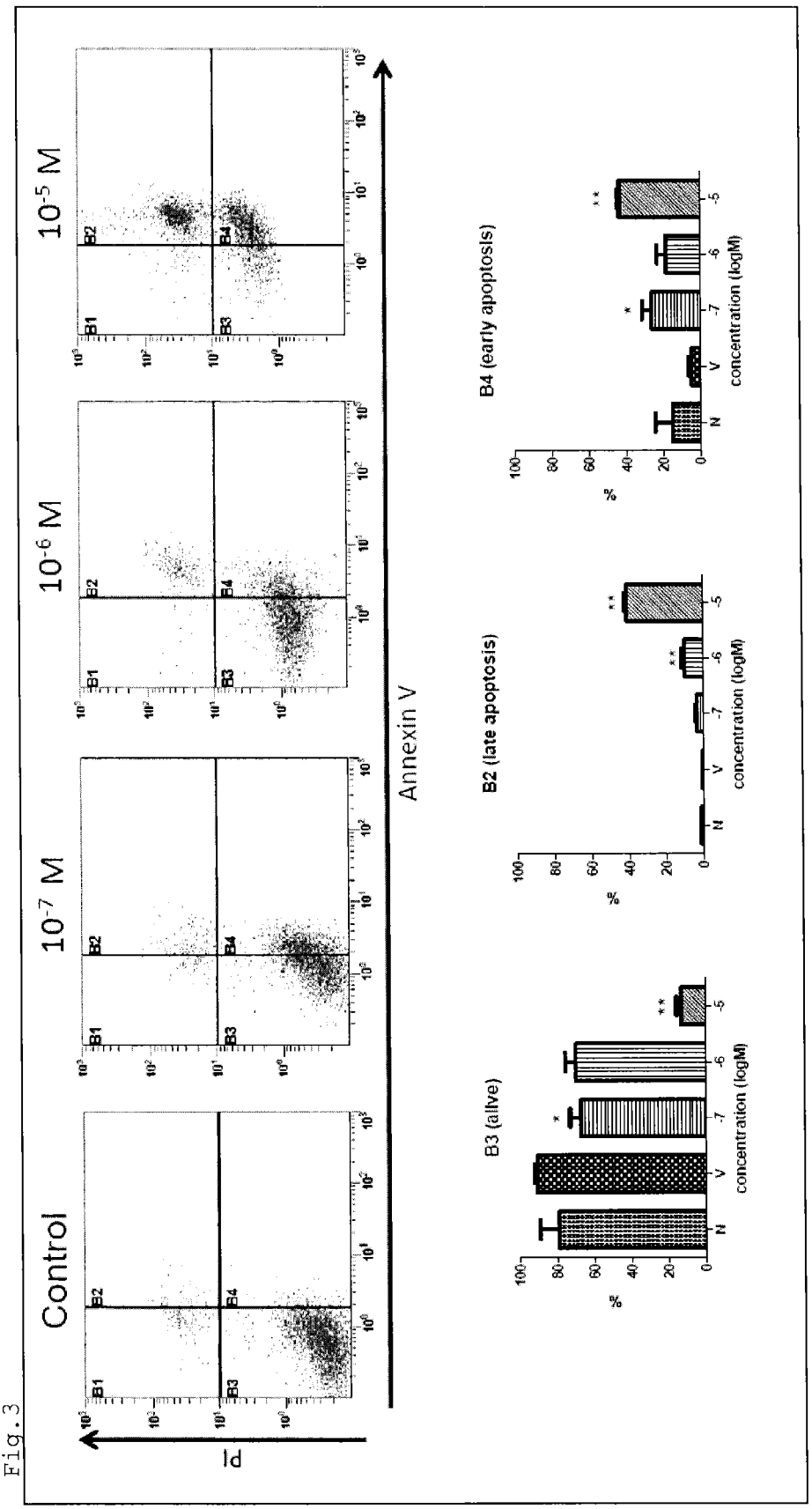
FIG. 3 shows that a compound of the present invention (HS-2) induced apoptosis of IMR-32 neuroblastoma cells.

As a result, the compound (HS-2) showed a concentration-dependent ability to induce apoptosis and had a significant apoptosis-inducing effect at 10 μM. FIG. 3 shows the results.

As a result, the compound of the present invention had strong antitumor activity at a concentration as low as $10^{-7}$ M. The activity was found to be selective for tumor cells over normal cells ($IC_{50}$ values for normal cells: 1.75 μM for HUVEC, 61.4 μM for NHDF), and apoptosis was found to be involved in this mechanism.

The invention claimed is:

1. An indirubin derivative of formula (1) or a salt thereof:

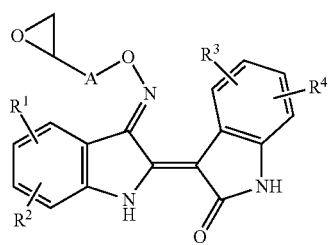

(1)

wherein A is an alkylene group having 1 to 4 carbon atoms, and $R^1$ to $R^4$ are each independently a hydrogen atom, a halogen atom, a hydroxy group, or an alkoxy group.

2. The indirubin derivative or a salt thereof according to claim 1, wherein A is a methylene group.

3. The indirubin derivative or a salt thereof according to claim 1, wherein $R^1$, $R^2$, $R^3$ and $R^4$ are each independently a hydrogen atom or an alkoxy group.

4. A pharmaceutical composition, comprising the indirubin derivative or a salt thereof according to claim 1 as an active ingredient.

5. An agent, comprising the indirubin derivative or a salt thereof according to claim 1 as an active ingredient, wherein the agent is suitable for treating liver cancer or neuroblastoma.

6. An agent, comprising the indirubin derivative or a salt thereof according to claim 1 as an active ingredient, wherein the agent is suitable for inducing apoptosis.

7. A pharmaceutical composition comprising the indirubin derivative or a salt thereof according to claim 1 and a pharmaceutically-acceptable carrier.

8. A method of treating liver cancer or neuroblastoma, comprising administering an effective amount of the indirubin derivative or a salt thereof according to claim 1.

9. A method of inducing apoptosis, comprising administering an effective amount of the indirubin derivative or a salt thereof according to claim 1.

10. The indirubin derivative or a salt thereof according to claim 2, wherein $R^1$, $R^2$, $R^3$, and $R^4$ are each independently a hydrogen atom or an alkoxy group.

* * * * *